United States Patent
Viviroli

(10) Patent No.: US 10,551,337 B2
(45) Date of Patent: Feb. 4, 2020

(54) DEVICE FOR PROCESSING CABLES

(71) Applicant: Komax Holding AG, Dierikon (CH)

(72) Inventor: Stefan Viviroli, Horw (CH)

(73) Assignee: KOMAX HOLDING AG, Dierikon (CH)

(*) Notice: Subject to any disclaimer, the term of this patent is extended or adjusted under 35 U.S.C. 154(b) by 583 days.

(21) Appl. No.: 15/198,028

(22) Filed: Jun. 30, 2016

(65) Prior Publication Data

US 2017/0023510 A1    Jan. 26, 2017

(30) Foreign Application Priority Data

Jul. 20, 2015    (EP) .................................... 15177555

(51) Int. Cl.
*G01N 27/22*    (2006.01)
*G01R 19/155*    (2006.01)
*H02G 1/12*    (2006.01)

(52) U.S. Cl.
CPC ........... *G01N 27/22* (2013.01); *G01R 19/155* (2013.01); *H02G 1/1256* (2013.01)

(58) Field of Classification Search
None
See application file for complete search history.

(56) References Cited

U.S. PATENT DOCUMENTS

| | | | | |
|---|---|---|---|---|
| 2,774,858 A | * | 12/1956 | Heilshorn | B23K 11/06 219/119 |
| 4,095,078 A | * | 6/1978 | Waenerlund | B23K 11/22 219/68 |
| 4,520,229 A | | 5/1985 | Luzzi et al. | |
| 4,815,207 A | * | 3/1989 | Schwartzman | H02G 1/1212 269/275 |

FOREIGN PATENT DOCUMENTS

| | | |
|---|---|---|
| DE | 10001129 A1 | 7/2001 |
| EP | 1515403 A2 | 3/2005 |
| EP | 1772701 A1 | 4/2007 |
| EP | 2717399 A1 | 9/2014 |
| JP | H02133016 A | 5/1990 |
| JP | H11299036 A | 10/1999 |
| JP | 2000354315 A | 12/2000 |
| WO | 2004095894 A1 | 11/2004 |

OTHER PUBLICATIONS

Asahi Seiki KK; Method for detecting cut depth by cutting blade into covered wire and coat peeling device therefor; Dec. 19, 2000; Goto Ryota; JP 2000354315 A.*

* cited by examiner

*Primary Examiner* — Nasima Monsur

(74) *Attorney, Agent, or Firm* — William J. Clemens; Shumaker, Loop & Kendrick, LLP

(57) ABSTRACT

A device for processing—particularly stripping insulation, cutting, contacting, fitting-out, connecting, measuring or checking—a cable that has at least one insulated electrical conductor includes a metal tool movable relative to the cable and a measuring device by which contact with the electrical conductor by the tool is detectable. The tool is connected with a first electrode body movable relative to a second electrode body so that through the two electrode bodies, which bodies are separated from one another by an air gap or an insulating material, a coupling capacitor is formed, by which the metal tool is or can be coupled to the measuring device, to an alternating voltage source or to an electrical potential.

16 Claims, 7 Drawing Sheets

DEVICE FOR PROCESSING CABLES

FIELD

The invention relates to a device for processing, particularly stripping insulation, cutting, contacting, fitting-out, connecting, measuring or checking, cables which comprise at least one metal conductor which is enclosed by an insulation layer, in a given case a cable casing.

BACKGROUND

For connection of electrical modules use is made of cables which are typically connected by means of plug contacts, plug connectors or soldered connections with terminals of an associated electrical module and for this purpose are previously stripped of insulation at the ends. On occasion, cable parts are connected together by splicing devices such as known from, for example, U.S. Pat. No. 4,520,229 A.

EP 1515403 A2 discloses a cable processing machine with a cable advance device and two pivot arms, which can feed the leading and trailing ends of a cable length by means of grippers to processing stations, crimping presses or bushfitting devices arranged laterally of the cable longitudinal axis. The cable is separated off beforehand by means of separating or stripping knives and stripped of insulation at the ends. In that case attention has to be given avoidance of damage of the electrical conductors by the tool or the stripping knife during the stripping of insulation.

EP 2717399 A1 discloses a method for stripping insulation from a cable extending in longitudinal direction, in which an insulation is cut into by means of stripping knives and subsequently pulled off by displacing the stripping knives in longitudinal direction. During the pulling-off process the longitudinal position of the stripping knives is registered in each instance at the points at which the stripping knives contact the cable conductors. Due to the number of registered longitudinal positions or places of conductor contact the stripped cable has a high quality.

In order to detect contact with conductor a measuring device equipped with a capacitive sensor is used. The capacitive sensor is connected with the stripping knives and constructed in such a way that contact of the conductive knife with the conductor of the cable can be detected on the basis of an increase in capacitance.

FIG. 1 shows a prior art correspondingly designed device 1' for stripping insulation from cables, which is provided with a measuring device 6 serving for capacitance measurement. For that purpose, the measuring device 6 is connected with the stripping knife 10' by way of a screened measurement cable 90, plug connector 91 and contacting plate 92. The stripping knife 10' serves as a first electrode of a capacitor, the second electrode of which is formed by the mass of the stripping device. If during the work process the stripping knife 10' penetrates the casing or insulation 82 of the processed cable 8 and comes into contact with the electrical conductor 81 the capacitance correspondingly increases. Consequently, through measuring the resulting capacitance changes it is possible to detect contact with the electrical conductor 81 by the stripping knife 10'.

The electrically equivalent circuit diagram of the device 1' of FIG. 1 with respect thereto is shown in FIG. 2. The stripping knife 10' has, without cable contact, a capacitance CW relative to ground potential M. The cable 8 or the electrical conductor 81 has a conductor capacitance CL relative to ground potential M. As soon as the stripping knife 10' contacts the cable conductor 81, the switch S1 shown in FIG. 2 is closed, as a result of which the capacitances CW of the stripping knife 10' and CL of the cable conductor 81 are added together. If the cable conductor 81 should make contact with the mass (ground potential M) of the stripping device 1' then the switch S2 shown in FIG. 2 is closed. The capacitor CG represents the basic capacitance of the device 1'.

During operation of the device the measurement cable 90 is moved and deformed by any movement of the stripping knife 10' connected therewith, which requires a complicated cable guidance and can lead to cable fractures and produce changes in capacitance, which influence the measurement. Insofar as the stripping knife 10' has to be demounted and reinstalled for servicing and re-equipped purposes then the measurement cables 90 have to be unplugged and plugged back in again on each occasion. This leads to a corresponding expenditure of time and can give rise to errors if the measurement cables 90 are erroneously swapped or no longer plugged in. High-quality plug connectors 91 and screen measurement cables 90 additionally occasion a relatively high outlay of cost and assembly effort for production of the stripping device 1'.

Moreover, the cables connected with the tool impair the mobility of the tool. In particular, multiple rotations in the same axis can hardly be realized.

In the case of stripping devices with rotating parts, particularly rotating knives, there is additionally the problem that a fixed cabling, in technical terms, is barely able to be realized. The stated problems remain regardless of whether the tool is moved linearly or along a curve.

The described problems are not confined to stripping devices, but arise with all devices for processing cables and conductors in which a tool connected with a cable is moved.

EP 1772701 A1 discloses, for example, a device for determining the diameter of the electrical conductor of a cable, which is acted on at a first position by an alternating voltage signal, which is decoupled again at a second position by means of a capacitive sensor and supplied to a measuring device. In order to determine the conductor diameter, displaceably mounted tools, contact elements or contact knives, which are connected with a defined electrical potential by way of a connecting cable, are guided towards the electrical conductor until this is contacted and the alternating voltage signal experiences a change, whereby the conductor diameter can be established.

In the case of this device as well, the cables connected with the tool are subjected to a mechanical loading and occasion corresponding outlay in production and maintenance. The tool is similarly limited in mobility.

SUMMARY

The present invention therefore has an object of overcoming the disadvantages of the prior art and indicating an improved device for processing, particularly for stripping insulation, cutting, contacting, fitting-out, connecting, measuring or checking, a cable which comprises at least one insulated electrical conductor.

In particular, an improved device for processing a cable with an electrical conductor is to be indicated, which is to be contacted or not contacted during the cable processing, wherein the desired or undesired contacting of the electrical conductor advantageously shall be measurable.

Restrictions, particularly restrictions with respect to the mobility of the tool, to which the known devices are subject shall be avoided. The tool shall be freely movable and, in particular, rotatable as often as desired about an axis.

The device according to the invention shall be producible in simple manner and with reduced costs and be able to be maintained with a reduced outlay.

In operation of the device, influences disturbing the measurement result shall be largely avoided or be able to be eliminated by simple measures.

The device, which serves for processing, particularly stripping insulation, cutting, contacting, fitting-out, connecting, measuring or checking, a cable which has at least one insulated electrical conductor, comprises a tool movable relative to the cable and a measuring device by means of which contacting of the electrical conductor by the tool is detectable.

According to the invention the tool is connected with a first electrode body which is movable relative to a, preferably stationary, second electrode body so that through the two electrode bodies, which are separated from one another by an air gap or an insulation material, a coupling capacitor is formed by way of which the metal tool is or can be coupled to the measuring device, to an alternating voltage source or to an electrical potential.

The device according to the invention can be realized in different configurations without the tool having to be connected by means of one or more cables with associated cable terminals, for example, a measuring device, a voltage source or an electrical potential, for example ground. It is thus possible to dispense with cables for contacting the tool and the mounting of such cables, for which reason costs and maintenance effort are correspondingly reduced.

The first and second electrode bodies are made of metal and preferably each coated at least partly with a sliding plastics material coating so that a slide bearing is formed. The insulating plastics material coatings shall have a high slide capability and preferably consist of the materials sold under the trademarks TEFLON, ERTALON PA, NYLATRON, ERTACETAL POM, ERTALYTE PET, ERTALYTE TX or HOSTAFORM. For preference, plastics materials with a high dielectric constant are used.

The coupling capacitor can thus be advantageously integrated in a mounting device, particularly a slide bearing, suitable for holding the tool.

The solution according to the invention allows realization of the device in different embodiments. In basic embodiments of the device the measuring device is constructed:
a) for measuring changes in the capacitance of the tool which arise if the tool comes into contact with the electrical conductor of the cable or
b) for monitoring an alternating voltage signal which at a first position can be coupled into the electrical conductor and at further positions decoupled from the electrical conductor and on the one hand can be fed to the measuring device and on the other hand, as soon as the tool contacts the electrical conductor, to an electrical potential by way of the coupling capacitor or
c) for monitoring an alternating voltage signal, which, by way of the coupling capacitor and the tool, can be coupled into the electrical conductor at a first position and decoupled from this at a second position and fed to the measuring device.

The coupling capacitor can therefore advantageously be used in different forms so as to connect the tool with an element of the electrical circuit arrangement.

The first and second electrode bodies are preferably so dimensioned and guided relative to one another that congruent surfaces of the two electrode bodies and the mutual spacing thereof during the mutual rotation and/or displacement of the two electrode bodies remains at least approximately constant. Thus, the capacitance of the coupling capacitor also remains substantially constant and the measurement of the capacitance of the tool is largely unaffected by the movement thereof.

However, in order to be able to completely exclude any residual disturbing influences on the measurement the course of the capacitance of the coupling capacitor is registered for a full movement cycle of the tool. Appropriate compensation for non-linearities in the course of the coupling capacitance can be made at the time of evaluation of measurement signals. For example, use can be made of an encoder or rotational angle transmitter which during registration of the course of the capacitance and during later operation of the device indicates the respective angular position of the tool so that the capacitance of the coupling capacitor can be detected as a function of the instantaneous angular position of the tool and taken into consideration in the calculation of the measurement results.

In a preferred embodiment the first electrode body is of drum-shaped construction and rotatably mounted by a drive device within the second electrode body, which is of annular or hollow-cylindrical construction.

The drive device, by means of which the tool is rotated, preferably comprises a drive shaft which rotatably mounts the first electrode body. The drive shaft can be mounted in the slide bearings optionally formed by the electrode bodies and/or in a separate bearing block.

For preference, through the bearing shaft there is prevention of occurrence of an electrical connection between the first and second electrode bodies. Insofar as the bearing shaft is electrically coupled with the first electrode body and also with the bearing block this is preferably separated from the second electrode body by a first insulation layer. The tool is preferably driven by means of an insulating drive belt, which mechanically couples the drive shaft with, but electrically insulates it from, a drive motor.

For insulation of the second electrode body relative to ground, this is preferably separated by a second insulation layer from a mounting element which supports the device. The said mounting element can be, for example, a base plate or a device base.

The first electrode body preferably mounts a tool holder into which the at least one tool is inserted. In addition, a setting device by means of which the tool holder and tool are actuable is preferably provided in the first electrode body. For example, the tool holder comprises two rotatably mounted levers, at the front ends of which are provided blades or stripping knives which are directed towards one another and which on actuation of the setting device are moved towards or apart from one another.

In further preferred embodiments the tool is integrated in the first electrode body or integrally connected therewith. The tool can also itself form the first electrode body.

The tool is, for example, constructed as a roller-shaped first electrode body by means of which the cable can be scanned so as to detect, in particular, places at which the cable has an anomaly, such as a spliced connection, an insulation weakness or an insulation interruption. As soon as the roller-shaped first electrode body contacts the electrical conductor an abrupt change in the measured capacitance of the tool takes place. However, even capacitance changes which do not occur abruptly can be detected by means of the measuring device. If the thickness of the insulation layer or of the cable casing varies due to a production error this can be established on the basis of the measured capacitance changes. Spliced connections can be detected in the same way, since in the case of these either a connection with the electrical conductor in conjunction with an increase in the tool capacitance or an increase in the diameter in conjunction with a reduction in the tool capacitance arises.

The roller-shaped first electrode body is preferably rotatably mounted in the second electrode body, which for its part is constructed as a stationary bearing shell. A metal second roller body is preferably provided, which is rotatably mounted in a metal second bearing shell and insulated relative to this second bearing shell, which is preferably connected with ground potential, so that a roller pair is formed which is suitable for guidance of and contact-making with the cable on both sides. In the case of contacting of the electrical conductor by both rollers, the change in capacitance correspondingly doubles.

The at least one tool is designed as required in correspondence with the kind of processing. Advantageously at least one stripping knife is provided for stripping insulation, cutting, fitting-out and contacting the cable, the electrical conductor or the cable insulation. Preferably at least two tools or knives, which may be identical, are provided. The knives are optionally rotatable, so that incisions longitudinally of and transversely to the cable axis can be performed.

Contact knives, contact pins, contact points or rollers are preferably provided for contacting, measuring or checking the cable, the electrical conductor or the cable insulation. In addition, pincers and shearing elements can be used as tools.

The measuring device according to the invention, which is provided with at least one processor, optionally a signal processor, memory units, interface units and preferably communication units, preferably also comprises control means making it possible to control the device in dependence on the determined measurement values. The determined measurement values are preferably processed and evaluated by the measuring device with consideration of the status of the control means.

DESCRIPTION OF THE DRAWINGS

The device according to the invention is described by way of example in the following in preferred embodiments with reference to drawings, in which.

DETAILED DESCRIPTION

Figure 1:
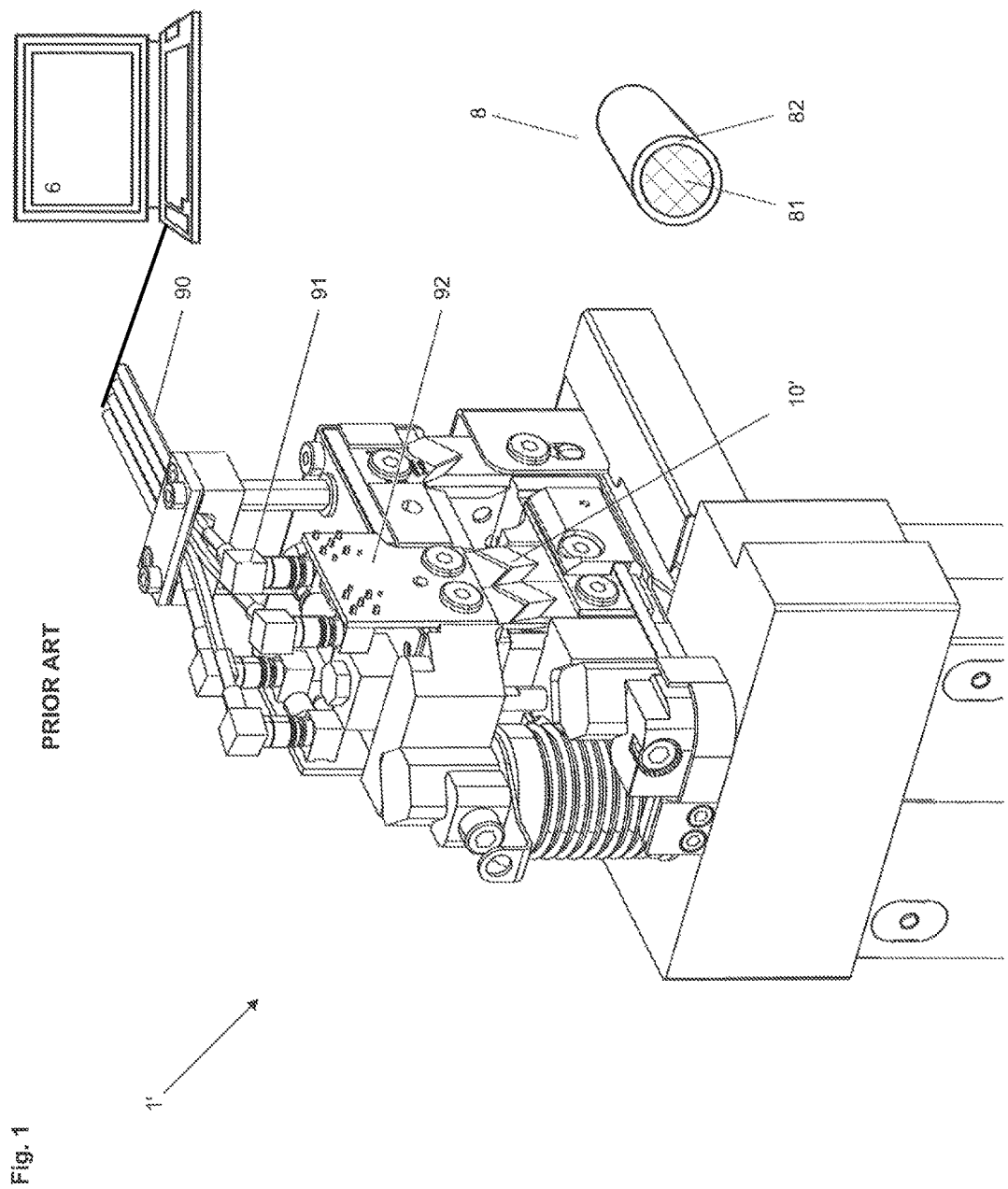
FIG. 1 shows the known stripping device 1', which was mentioned in the introduction and in which a measuring device is connected by way of measurement cables, plug connectors and a contact plate on either side with a respective stripping knife.

FIG. 1 shows the known stripping device 1', which is described in the introduction and in which a measuring device 6 is connected on either side with a respective stripping knife 10' by way of measurement cables 90, plug connectors 91 and a contact plate 92. Additionally shown are the measuring device 6, which is connected with the measurement cables 90, and a cable 8, which comprises an electrical conductor 81 and a cable casing 82.

Figure 2:
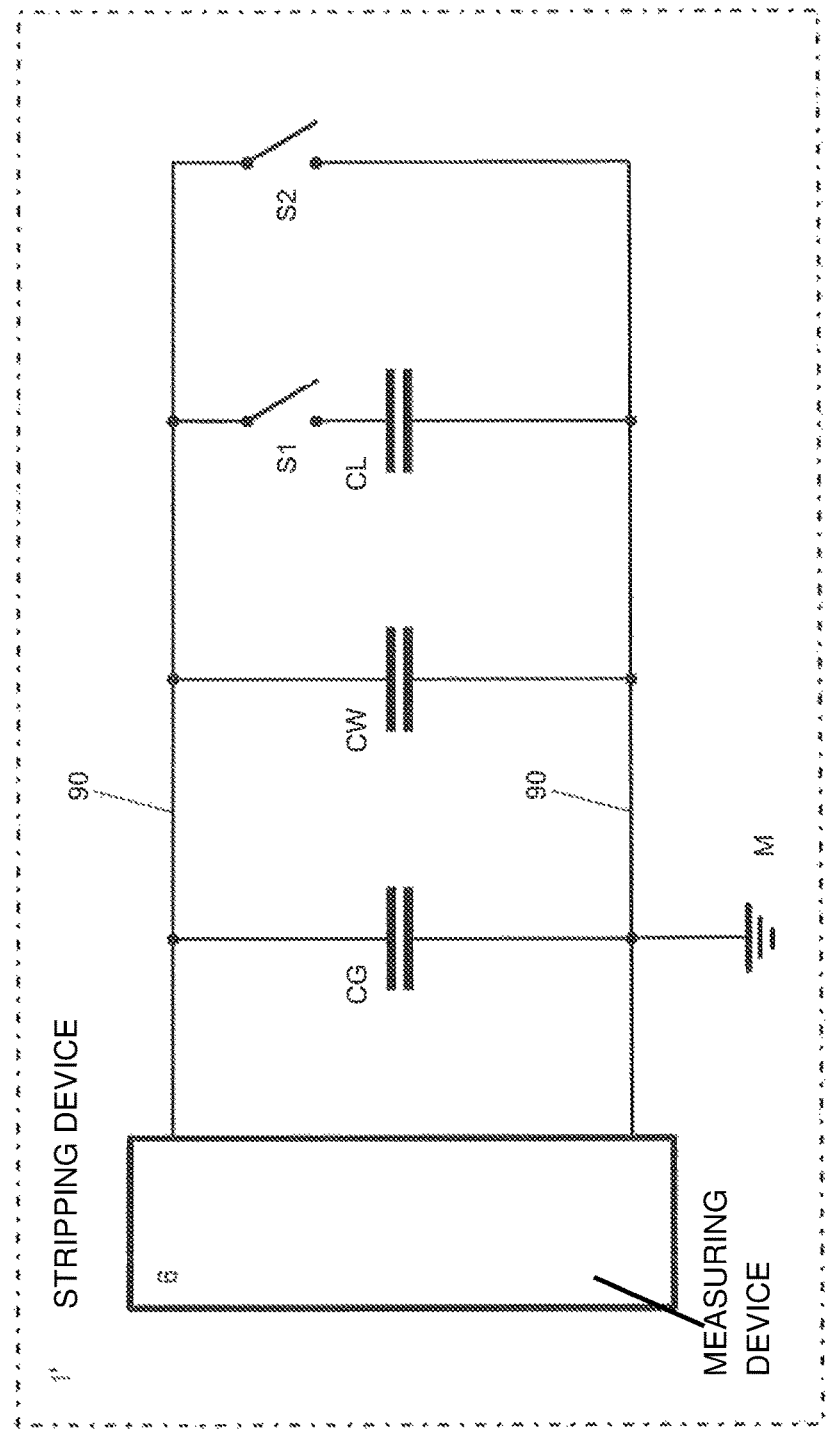
FIG. 2 shows an electrical equivalent circuit diagram of the stripping device of FIG. 1 with the measuring device and the capacitances connected therewith.

FIG. 2 shows the electrical equivalent circuit diagram of the stripping device 1' of FIG. 1 as described in the introduction.

Figure 3:
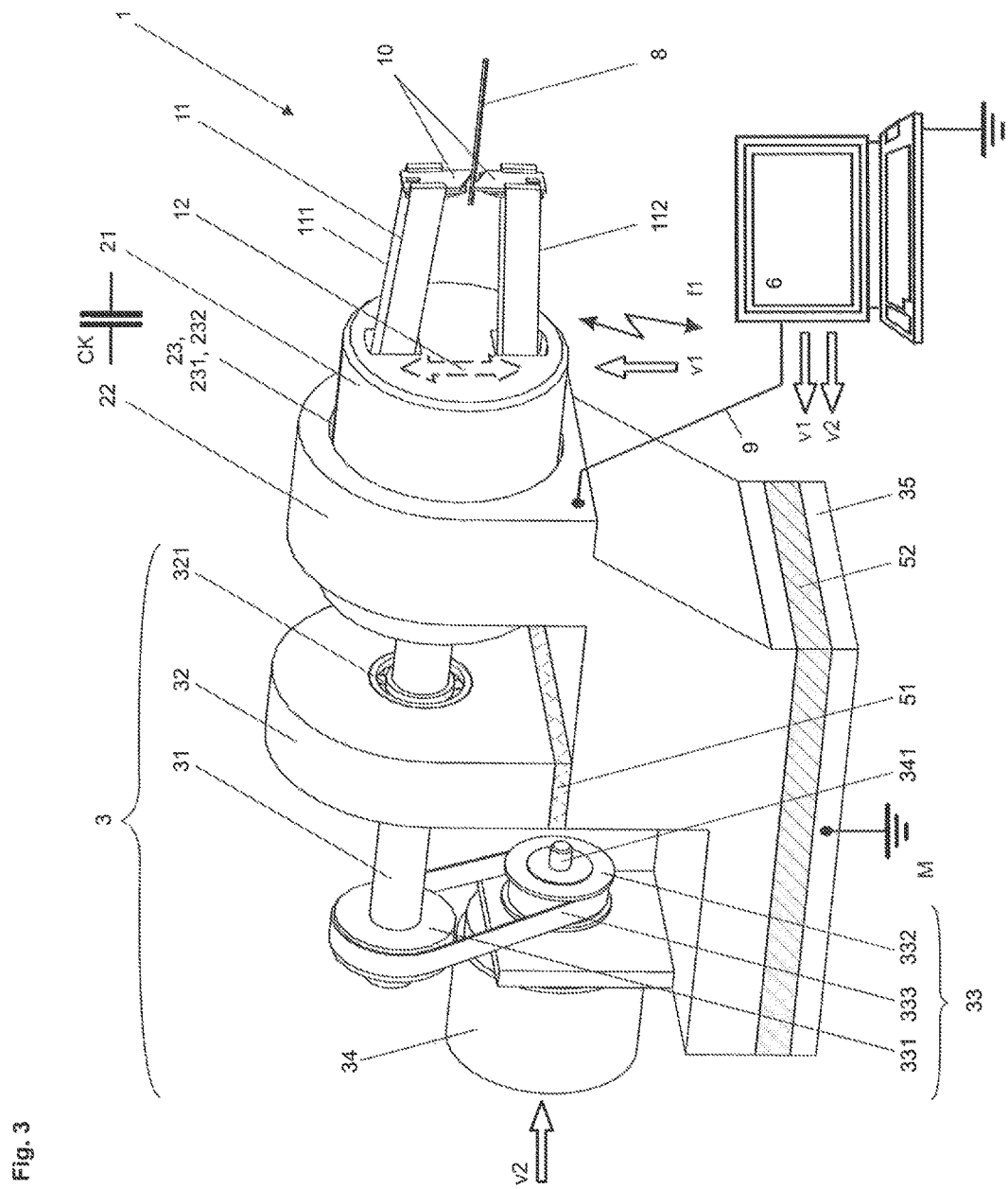
FIG. 3 shows a device according to the invention for processing or stripping a cable, which device comprises a stationary electrode body and a rotatably mounted moved electrode body provided with stripping knives, the two bodies forming a coupling capacitor.

FIG. 3 shows a device 1 according to the invention for processing or stripping a cable 8. The device 1 comprises a moved first electrode body 21, which is rotatably mounted within a stationary second electrode body 22 by a drive shaft 31 of a drive device 3. The two electrode bodies 21, 22 are electrically isolated from one another and form a coupling capacitor CK. The drive shaft 31, which is rotatably mounted within a bearing block 32 by means of a ball bearing 321, at the front end mounts the first electrode body 21 and at the rear end mounts a first gearwheel 331 of a transmission 33, which is coupled by way of a drive belt 333 with a second gearwheel 332. The second gearwheel 332 is connected with the motor shaft 341 of a drive motor 34. In order that the electrical isolation of the electrode bodies 21, 22 is not impaired by the drive device 3, the bearing block 32 is separated from the second electrode body 22 by a first insulation layer 51. In addition, the drive belt 333 preferably consists of an insulating material. Alternatively or additionally the gearwheels 331, 332 can also be made of an insulating material. The second electrode body 22 is electrically isolated from a mounting element or the device base 35 by a second insulation layer 52.

The first electrode body 21 is of drum-shaped construction and comprises a tool holder 11 with two tool levers 111, 112, which at the front end each mount a respective stripping knife 10. In addition, arranged in the first electrode body 21 is a setting device 12 which is shown schematically in FIG. 3 and by means of which the tool levers 111, 112 can be guided towards one another so as to cut into and in a given case pull off an insulation layer or the cable casing of a cable 8. The stripping knives 10 are preferably electrically coupled with the first electrode body 21 by the tool holder 11.

The two electrode bodies 21, 22 are preferably separated from one another by an air gap 23. However, the mutually facing surfaces of the two electrode bodies 21, 22 can also be coated with slidable plastics material layers 231, 232 which slidingly bear against one another. A slide bearing rotatably mounting the first electrode 21 is thereby formed. In this case, it is also possible to dispense with the mounting by the bearing block 32 and the device 1 can be dimensioned to be smaller.

In order to be able to detect contact of the electrical conductor 81 of the cable 8 by the stripping knives 10 the capacitance of the tools 10 relative to potential M is measured. For that purpose the stripping knives 10 are capacitively coupled by way of the capacitor CK and additionally by way of a connecting line 9 to the measuring device 6.

The measuring device 6 is preferably constructed as a measuring and control device and comprises, for preference, control modules by means of which the device 1, in particular the setting device 12 and the drive motor 34, is controllable. Control lines are symbolized in FIG. 3 by arrows v1, v2.

Figure 4:
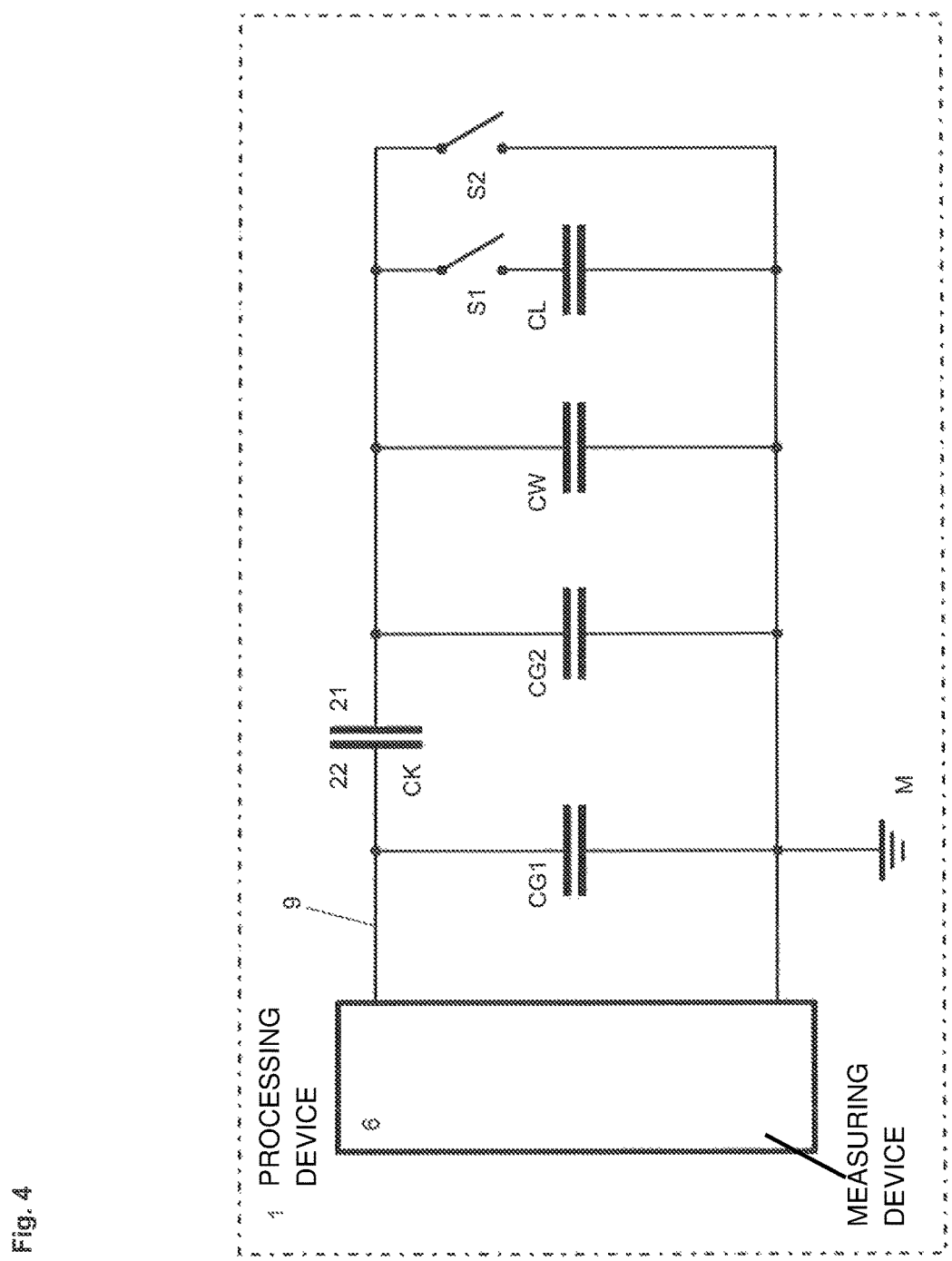
FIG. 4 shows an electrical equivalent circuit diagram of the stripping device of FIG. 3 with the measuring device and capacitances connected therewith.

FIG. 4 shows an electrical equivalent circuit diagram of the stripping device 1 of FIG. 3 with the measuring device 6 and capacitances connected therewith, the basic capacitance CG1 of the stationary parts of the device 1 which is connected by way of the coupling capacitor CK—which is formed by the two electrode bodies 21, 22—with the basic capacitance CG2 of the moved parts 11, 21, 31 of the device 1, the capacitance CW of the stripping knives 10 and the capacitance CL of the electrical conductor 81 of the cable 8 if the tool 10 contacts the electrical conductor 81 and the switch S1 accordingly is closed. Insofar as the knife 10 or the electrical line 81 comes into contact with ground M, the switch S2 is closed.

Insofar as the switches S1 and S2 are open, the total capacitance=CG1+(CK*(CG2+CW))/(CK+CG2+CW).

Insofar as the switch S1 is closed, the total capacitance=CG1+(CK*(CG2+CW+CL))/(CK+CG2+CW+CL).

The resulting capacitance in the case of opening or closing the switch S1 is preferably measured by means of a circuit arrangement comprising a measuring bridge with two bridge branches.

The capacitance to be measured is connected with the first bridge branch and a reference capacitance is connected with the second bridge branch, as is described in, for example, DE 10001129 A1. The reference capacitance is preferably selected in such a way that the bridge is unbalanced when the switch S1 is open. As soon as the tool 10 contacts the electrical conductor 81 and the switch S1 is accordingly closed, the measured capacitance increases and the measuring bridge comes out of equilibrium.

A variable reference capacitance set in correspondence with the overall capacitance when the switch S1 is open is preferably selected.

The solution according to the invention with realization of a coupling capacitor CK connected with the moved tool 10 can advantageously be implemented in various ways.

Figure 5:
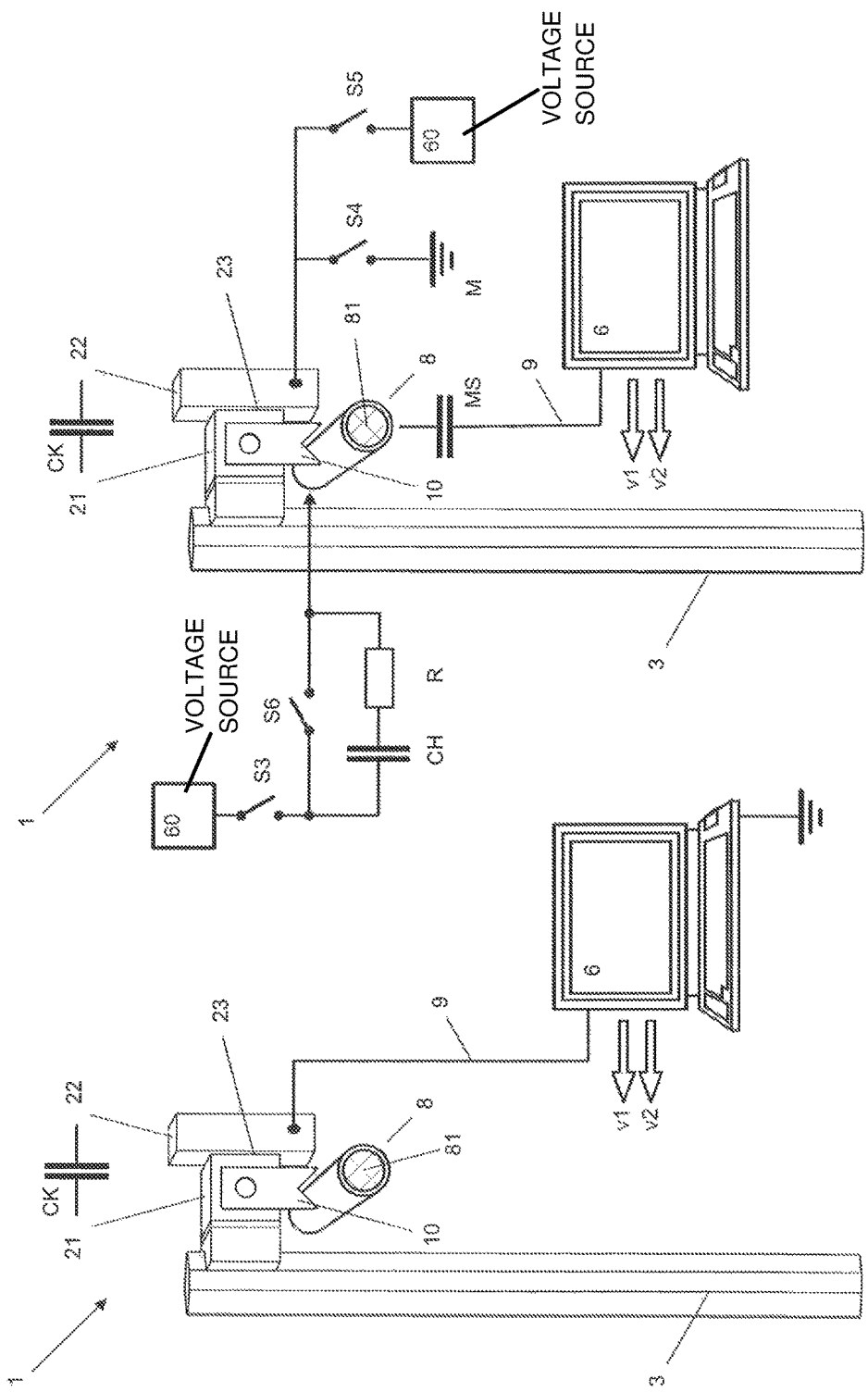
FIG. 5a shows a device according to the invention for processing or stripping a cable, which device comprises a stationary electrode body and a moved electrode body which is displaceably mounted thereon and provided with stripping knives, the bodies forming a coupling capacitor.
FIG. 5b shows the device of FIG. 5a, in which the measuring device monitors changes in an alternating voltage signal, which is coupled by an alternating voltage source into the electrical conductor of a cable either directly or by way of the coupling capacitor and the stripping knife.

FIG. 5a shows a device 1 according to the invention for processing a cable 8, which comprises a stationary electrode body 22 and a moved electrode body 21, which is displaceably mounted thereon and provided with stripping knives 10, the bodies forming a coupling capacitor CK. The moved first electrode body 21 can, for example, be moved upwardly and downwardly by means of a spindle or rack. In the case of contact of the electrical conductor 81 by the tool 10 the measured capacitance increases as has been described with reference to FIG. 3. The tool 10 can therefore be displaced together with the first electrode body 21 in desired manner linearly or along any desired curve. In that case, it has to be ensured that the capacitance of the coupling capacitor CK remains constant or correct compensation is provided for changes. For that purpose the first electrode body 21 is displaced over the entire path from one to the other abutment and at the same time changes in the capacitance CK are registered, these being appropriately taken into consideration in the calculation of the overall capacitance. Apart from the changes in the capacitance CK, compensation can also be provided for other measurement influences caused by the movement.

FIG. 5b shows the device 1 of FIG. 5a, in which the measuring device 6 monitors changes in an alternating voltage signal, which is coupled from an alternating voltage source 60 into the electrical conductor 81 of a cable 8 either directly or by way of the coupling capacitor CK and the stripping knife 10. The device 1 can be selectably configured through actuation of switches S3, S4, S5 and S6.

In a first configuration, the third switch S3, the fourth switch S4 and the sixth switch S6 are closed. The alternating voltage signal delivered by an alternating voltage source 60 is applied by way of the third switch S3 and the sixth switch S6 to the electrical conductor 81 of the cable 8 and capacitively decoupled again by a measuring probe or a coupling capacitor MS and supplied to the measuring device 6. As soon as the tool 10 contacts the electrical conductor 81 the alternating voltage signal is applied by way of the coupling capacitor CK and the fourth switch S4 to ground M. The measuring device 6 registers the corresponding change in the signal component delivered by the measuring probe MS. In a preferred embodiment, the application of the alternating voltage signal to the electrical conductor 81 selectably takes place by way of a coupling capacitor and/or by way of a current limiting element. By way of example, in FIG. 5b the series circuit of an auxiliary capacitor CH and a resistor R is shown, which after opening of the sixth switch S6 connects the output of the alternating voltage source 60 with the electrical conductor 81.

In a second configuration the switches S3 and S4 are opened and a fifth switch S5 closed. The alternating voltage signal delivered by the alternating voltage source 60 is now applied by way of the fifth switch S5 and the coupling capacitor CK to the electrical conductor 81 as soon as the tool 10 contacts the electrical conductor 81. The alternating voltage signal coupled into the electrical conductor 81 is decoupled again by means of the measuring probe MS and supplied to the measuring device 6.

Figure 6:
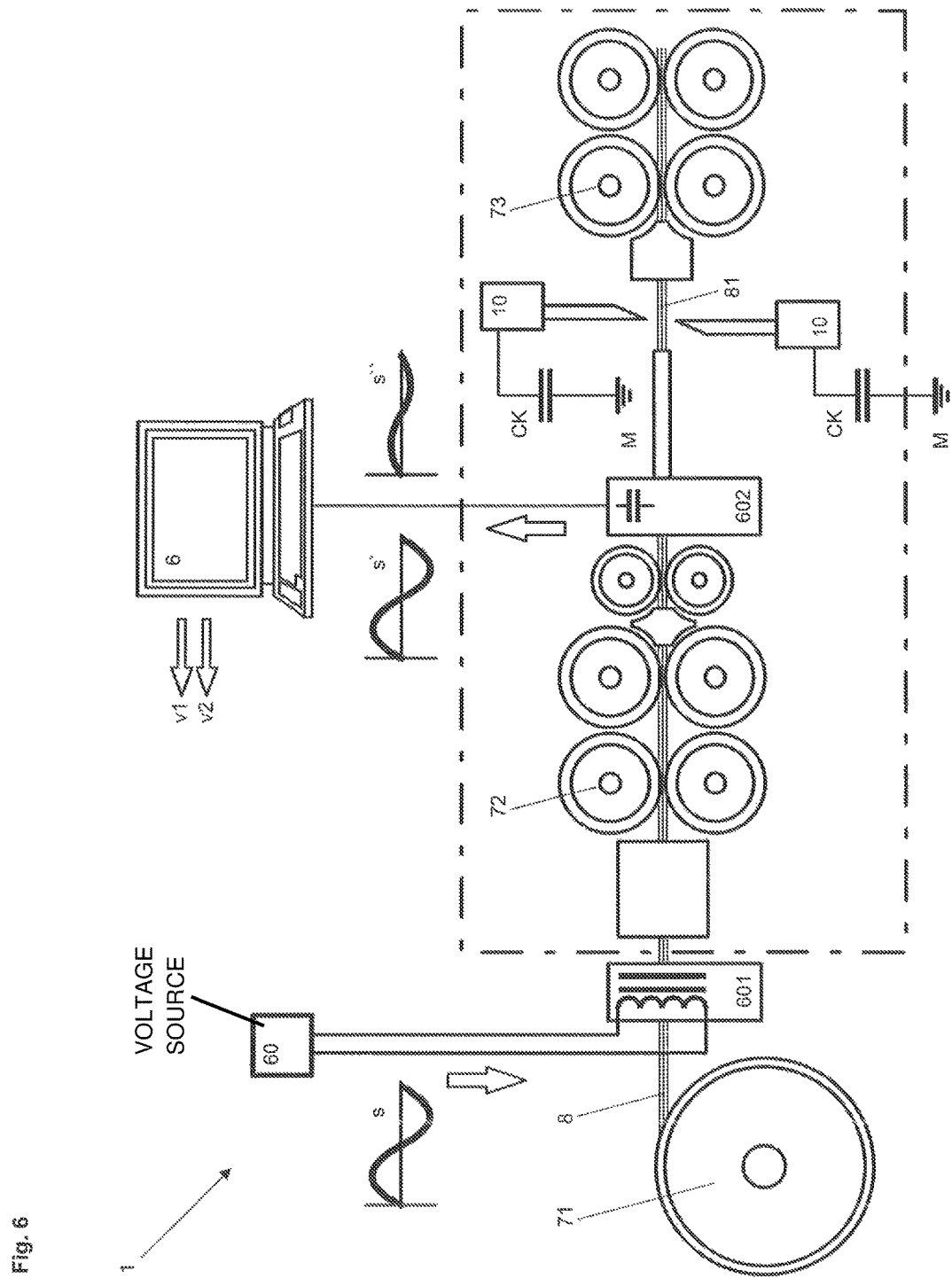
FIG. 6 shows the device in accordance with EP 1772701 A1 developed in accordance with the invention.

FIG. 6 shows the device 1, which is developed in accordance with the invention, according to EP 1772701 A1, this being usable for, inter alia, determination of the diameter of the electrical conductor 81 of a cable 8. The device 1 comprises a cable reel 71, from which cable 8 is unreeled and is led through the device 1 under guidance by entry rollers 72 and exit rollers 73. Provided in front of the entry rollers 72 is a coupling device 601 by way of which an alternating voltage signal s is coupled, preferably inductively, into the cable 8 at a first position. Provided between the entry rollers 72 and the exit rollers 73 is a decoupling device 602 by which the alternating voltage signal s' is decoupled, preferably capacitively, from the cable 8 at a second position and is fed to the measuring device 6.

For determination of the conductor diameter, displaceably mounted tools 10, contact elements or contact knives are provided, which are respectively connected by way of a coupling capacitor CK with a defined electrical potential, for example ground M. Realization of the coupling capacitor CK is effected by way of, for example, the device of FIG. 5b (switch S4 closed).

If the two tools 10 are guided towards the cable 8 and contact the electrical conductor 81 at a third position, a part of the alternating voltage signal is decoupled at this third position, for which reason the alternating voltage signal s" decoupled at the second position is correspondingly reduced. As a consequence, the diameter of the electrical conductor 81 can be determined by detection of the displacement position of the tools 10 at which the reduction in the alternating voltage signal s" has occurred. Insofar as the tools 10 are displaced through rotation of a spindle, for example by way of a step motor, the revolutions of the spindle can also be measured. FIG. 6 shows, by way of example, the coupled-in signal s, the non-reduced decoupled signal s' as well as the reduced decoupled signal s".

Figure 7:
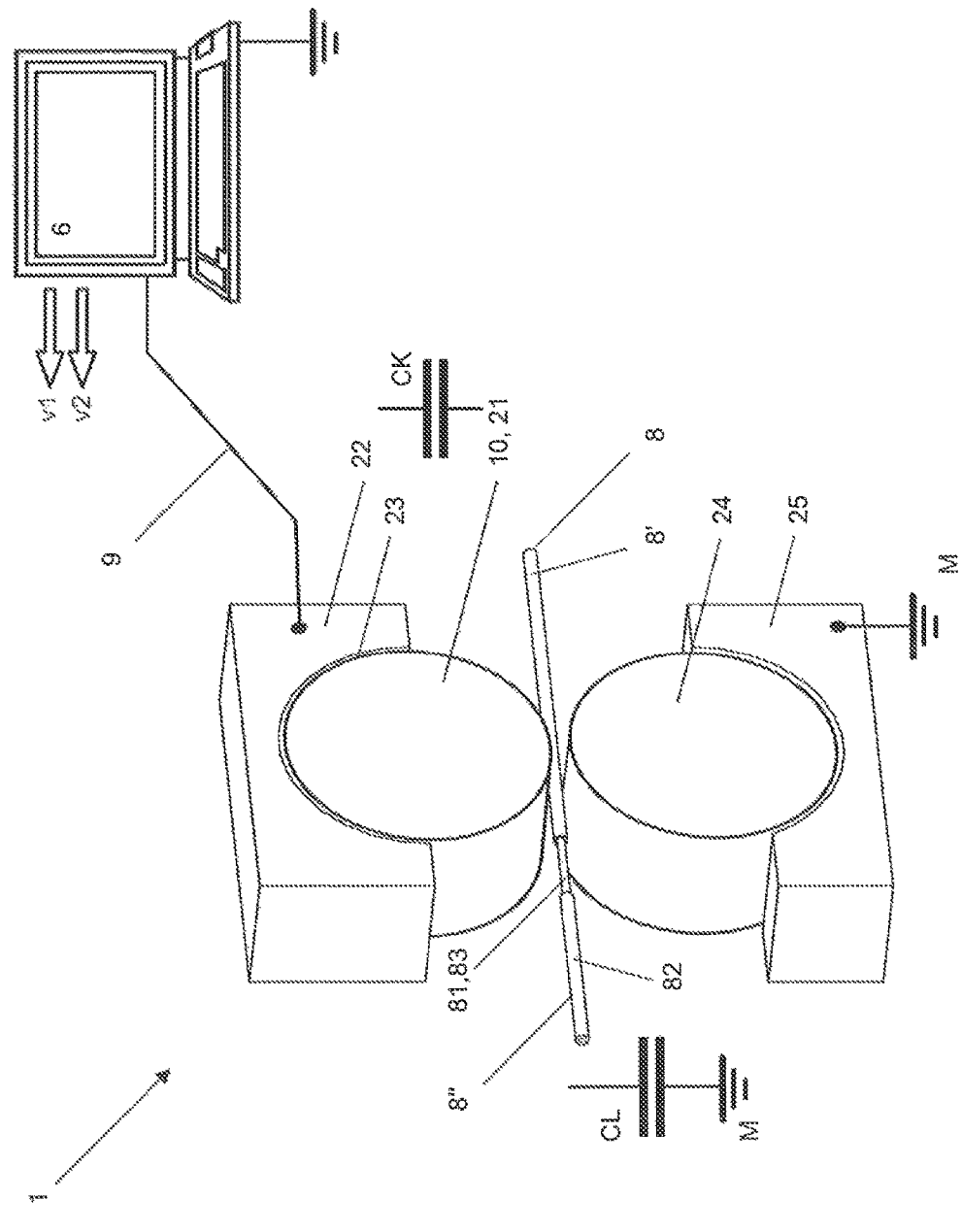
FIG. 7 shows a device according to the invention for processing a cable with an anomaly at a position at which the electrical conductor protrudes or a splice connecting the two cable parts together is provided.

FIG. 7 shows a device 1 according to the invention for processing a cable 8, which has an anomaly at a position at which the electrical conductor 81 protrudes or a splice 83 connecting two cable parts 8', 8" together is provided. The device 1 comprises a tool 10, which is constructed as a roller and serves at the same time as a moved first electrode body 21. The roller-shaped first electrode body 21 is rotatably mounted in a second electrode body 22 constructed as a stationary bearing shell. The two electrode bodies 21, 22 are separated from one another by an air gap 23 or slide elements or slide layers and form the coupling capacitor CK. When contact with the electrical conductor 81 takes place, a capacitance change again occurs and can be detected by the measuring device 6, which is connected with the second electrode body 22 by way of a connecting line 9. As soon as the depth of the insulation 82 changes, corresponding changes in capacitance can also be detected without contact with the electrical conductor 81 being required. As has been described with reference to FIG. 5a, an alternating voltage signal can also be decoupled from the electrical conductor 81 and transmitted by way of the coupling capacitor CK to the measuring device 6.

In this preferred embodiment the roller-shaped first electrode body 21 forms—together with a metal second roller body 24 which is rotatably mounted in and insulated relative to a metal second bearing shell 25, the second bearing shell 25 preferably being connected with ground potential—a roller pair. The cable 8 is led through between the two rollers 21, 24 of the roller pair. Insofar as the two rollers 21, 24 now contact the electrical conductor 81, the change in capacitance doubles. If a splice 83 which is connected with the electrical conductor 81 is led through the two rollers 21, 24, this can be detected in the same way.

As the embodiments show, the tool has a high degree of mobility through use of the coupling capacitor and avoidance of measurement cables. Alternatively or additionally, an inductive coupling can also be provided between the two electrode bodies 21, 22. Energy and signals, particularly control signals and measurement signals, can be bidirectionally transmitted by way of the capacitive or inductive coupling. For example, an inductive coupling for transmission of energy, which enables autonomous operation of the moved first electrode body, is effected. The measurement is preferably carried out, as described, by way of the constant coupling capacitor CK. Moreover, control signals and checking signals can also be transmitted by way of a radio channel f1 (see FIG. 3) of a wireless network such as 'BLUETOOTH' between a communications unit in the first electrode body 21 and the measuring device 6.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A device for processing a cable having at least one insulated electrical conductor, the device including a tool movable relative to the cable and a measuring device for detecting contact with the conductor by the tool, comprising:
   a first electrode body connected with the tool;
   a second electrode body, the first electrode body being movable relative to the second electrode body wherein the first and second electrode bodies are separated from one another by an air gap or an insulation material to form a coupling capacitor by which the tool is coupled to the measuring device, to an alternating voltage source or to an electric potential, wherein the first and second electrode bodies are mounted to be rotatable or displaceable relative to one another, wherein the first and second electrode bodies are dimensioned and mounted such that congruent surfaces of the first and second electrode bodies and a mutual spacing thereof remain at least approximately constant during mutual rotation or displacement of the first and second electrode bodies; and
   wherein changes in the congruency of the surfaces or changes in the mutual spacing of the first and second electrode bodies that arise during the mutual rotation or displacement are registered in the measuring device and are compensated for by the measuring device.

2. The device according to claim 1 wherein the measuring device is constructed to perform one of:
   a) measurement of changes in a capacitance of the tool which arise when the tool comes into contact with the conductor;
   b) monitoring an alternating voltage signal generated by the alternating voltage source and coupled into the conductor at a first position and decoupled from the conductor at a second position and which signal is fed to the measuring device, wherein when the tool makes contact with the conductor, the conductor is connected with the electrical potential by the coupling capacitor; and
   c) monitoring an alternating voltage signal generated by the alternating voltage source and coupled into the conductor by the coupling capacitor and the tool at a first position when the tool makes contact with the conductor and decoupled from the conductor at a second position and supplied to the measuring device.

3. The device according to claim 1 wherein the first electrode body is drum-shaped and rotatably mounted by a drive device within the second electrode body, the second electrode body being annular or hollow-cylindrical shaped.

4. The device according to claim 3 wherein the drive device includes a drive shaft mounting the first electrode body to be rotatable and which is mounted in a bearing block separated by an insulation layer from the second electrode body, and which is coupled with a drive motor by an insulating drive belt.

5. The device according to claim 1 wherein the tool is an insulation stripping knife.

6. The device according to claim 1 wherein the second electrode body is separated by an insulation layer from a mounting element that supports the device.

7. The device according to claim 1 wherein the first electrode body mounts a tool holder into which the tool is inserted and includes a setting device for actuating the tool holder and the tool.

8. The device according to claim 1 wherein the tool is integrated in or integrally connected with the first electrode body or the tool forms the first electrode body.

9. The device according to claim 1 wherein the tool is formed as the first electrode body and is roller-shaped by which the cable is scanned to detect locations at which the cable has an anomaly.

10. The device according to claim 9 wherein the roller-shaped first electrode body is rotatably mounted in the second electrode body formed as a stationary bearing shell.

11. The device according to claim 9 including a metal roller body rotatably mounted in a metal bearing shell and insulated relative to the metal bearing shell connected with a ground potential, wherein the first electrode body and the metal roller body make contact with and guide the cable therebetween.

12. The device according to claim 1 wherein the first and second electrode bodies are made of metal and each are coated at least partly with a sliding synthetic material layer, wherein the first and second electrode bodies bear against one another at the synthetic material layers to form a slide bearing.

13. The device according to claim 1 wherein the tool is adapted for stripping insulation, cutting, contacting, fitting-out, measuring or checking the cable, the conductor or a cable insulation of the cable.

14. A device for processing a cable having at least one insulated electrical conductor, the device including a tool movable relative to the cable and a measuring device for detecting contact with the conductor by the tool, comprising:
   a first electrode body connected with the tool; and
   a second electrode body, the first electrode body being movable relative to the second electrode body wherein the first and second electrode bodies are separated from one another by an air gap or an insulation material to form a coupling capacitor by which the tool is coupled to the measuring device, to an alternating voltage source or to an electric potential, and wherein the first electrode body is drum-shaped and rotatably mounted by a drive device within the second electrode body, the second electrode body being annular or hollow-cylindrical shaped.

15. A device for processing a cable having at least one insulated electrical conductor, the device including a tool movable relative to the cable and a measuring device for detecting contact with the conductor by the tool, comprising:
   a first electrode body connected with the tool; and
   a second electrode body, the first electrode body being movable relative to the second electrode body wherein the first and second electrode bodies are separated from one another by an air gap or an insulation material to form a coupling capacitor by which the tool is coupled to the measuring device, to an alternating voltage source or to an electric potential, and wherein the tool is formed as the first electrode body and is roller-shaped by which the cable is scanned to detect locations at which the cable has an anomaly.

16. A device for processing a cable having at least one insulated electrical conductor, the device including a tool movable relative to the cable and a measuring device for detecting contact with the conductor by the tool, comprising:
   a first electrode body connected with the tool; and
   a second electrode body, the first electrode body being movable relative to the second electrode body wherein the first and second electrode bodies are separated from one another by an air gap or an insulation material to form a coupling capacitor by which the tool is coupled to the measuring device, to an alternating voltage source or to an electric potential, and wherein the first and second electrode bodies are made of metal and each are coated at least partly with a sliding synthetic material layer, wherein the first and second electrode bodies bear against one another at the synthetic material layers to form a slide bearing.

* * * * *